US008377126B2

(12) United States Patent  
McGee et al.

(10) Patent No.: US 8,377,126 B2
(45) Date of Patent: Feb. 19, 2013

(54) RENEWABLE POLYMERIC LENS COATING

(75) Inventors: Joseph A. McGee, Canandaigua, NY (US); David Paul Vanderbilt, Webster, NY (US); Paul L. Valint, Jr., Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 647 days.

(21) Appl. No.: 12/641,422

(22) Filed: Dec. 18, 2009

(65) Prior Publication Data

US 2010/0168855 A1 Jul. 1, 2010

Related U.S. Application Data

(60) Provisional application No. 61/203,883, filed on Dec. 30, 2008.

(51) Int. Cl.
*A61F 2/16* (2006.01)
(52) U.S. Cl. ................. 623/6.56; 623/6.62; 351/159.02
(58) Field of Classification Search ................. 623/5.16, 623/6.62, 6.56, 926; 351/159.02, 159.33
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,153,641 A | 5/1979 | Deichert et al. | |
| 4,197,266 A | 4/1980 | Clark et al. | |
| 4,304,705 A | 12/1981 | Heilmann et al. | |
| 4,378,411 A | 3/1983 | Heilmann et al. | |
| 4,485,236 A | 11/1984 | Rasmussen et al. | |
| 4,555,732 A | 11/1985 | Tuhro | |
| 4,695,608 A | 9/1987 | Engler et al. | |
| 4,740,533 A | 4/1988 | Su et al. | |
| 4,758,595 A | 7/1988 | Ogunbiyi et al. | |
| 4,910,277 A | 3/1990 | Bambury et al. | |
| 4,954,587 A | 9/1990 | Mueller | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,081,197 A | 1/1992 | Heilmann et al. | |
| 5,091,489 A | 2/1992 | Heilmann et al. | |
| 5,177,165 A | 1/1993 | Valint, Jr. et al. | |
| 5,219,965 A | 6/1993 | Valint, Jr. et al. | |
| 5,260,000 A | 11/1993 | Wandu et al. | |
| 5,271,875 A | 12/1993 | Appleton et al. | |
| 5,310,779 A | 5/1994 | Lai | |
| 5,321,108 A | 6/1994 | Kunzler et al. | |
| 5,344,701 A | 9/1994 | Gagnon et al. | |
| 5,352,714 A | 10/1994 | Lai et al. | |
| 5,358,995 A | 10/1994 | Lai et al. | |
| 5,364,918 A | 11/1994 | Valint, Jr. et al. | |
| 5,387,662 A | 2/1995 | Kunzler et al. | |
| 5,573,726 A | 11/1996 | Dassanayake et al. | |
| 5,652,014 A | 7/1997 | Galin et al. | |
| 5,804,318 A | 9/1998 | Pinchuk et al. | |
| 6,858,310 B2 | 2/2005 | McGee | |
| 7,832,856 B2 * | 11/2010 | Vanderbilt et al. | 351/159.02 |
| 7,988,988 B2 * | 8/2011 | Valint et al. | 424/427 |
| 8,100,528 B2 * | 1/2012 | Linhardt et al. | 351/159.73 |
| 2003/0166831 A1 * | 9/2003 | Shastri et al. | 528/422 |
| 2004/0142011 A1 * | 7/2004 | Nilsson et al. | 424/422 |
| 2007/0030443 A1 * | 2/2007 | Chapoy et al. | 351/160 R |
| 2007/0116740 A1 * | 5/2007 | Valint et al. | 424/428 |
| 2008/0151180 A1 * | 6/2008 | Vanderbilt et al. | 351/160 R |
| 2010/0168356 A1 * | 7/2010 | Lai et al. | 526/239 |
| 2012/0194779 A1 * | 8/2012 | Zhang et al. | 351/159.33 |

FOREIGN PATENT DOCUMENTS

| | | |
|---|---|---|
| EP | 0 392 735 | 7/1996 |
| WO | WO 96/31792 | 10/1996 |
| WO | WO 2004/081624 | * 9/2004 |
| WO | WO 2005/031442 | * 4/2005 |
| WO | WO2008/079495 | 7/2008 |

OTHER PUBLICATIONS

Lai, Yu-Chin, "The Role of Bulky Polysiloxanylalkyl Methacrylates in Polyurethane-Polysiloxane Hydrogels," Journal of Applied Polymer Science, vol. 60, 1193-1199 (1996).
U.S. Appl. No. 60/853,579, filed Oct. 23, 2006, Heiler.
U.S. Appl. No. 60/895,770, filed Mar. 20, 2007, Heiler.

* cited by examiner

*Primary Examiner* — Paul Prebilic
(74) *Attorney, Agent, or Firm* — John E. Thomas

(57) ABSTRACT

Disclosed are biomedical devices having a hydrophilic coating on a portion of a surface thereof, the biomedical device comprising: (a) a biomedical device obtained from a polymerization product of a monomeric mixture comprising (i) a polymerizable monomer containing a boronic acid moiety and an electron withdrawing moiety; and (ii) a biomedical device-forming comonomer; and (b) a hydrophilic reactive polymer having complementary reactive functionalities along the polymer chain, wherein the complementary reactive functionalities along the polymer chain of the hydrophilic reactive polymer of (b) bind with the boronic acid moieties of the biomedical device of (a), thereby producing a biocompatible coating which can be removed and re-applied to restore the surface properties of the biomedical device to substantially as-new condition. Methods for treating the biomedical device are also disclosed.

15 Claims, No Drawings

RENEWABLE POLYMERIC LENS COATING

This application claims the benefit of Provisional Patent Application No. 61/203,883 filed Dec. 30, 2008 which is incorporated by reference herein.

BACKGROUND OF THE INVENTION

1. Technical Field

The present invention generally relates to the surface treatment of biomedical devices such as contact lenses and medical implants.

2. Description of the Related Art

Ophthalmic devices such as contact lenses made from, for example, silicone-containing materials, have been investigated for a number of years. Such materials can generally be subdivided into two major classes, namely hydrogels and non-hydrogels. Hydrogels can absorb and retain water in an equilibrium state whereas non-hydrogels do not absorb appreciable amounts of water. Regardless of their water content, both non-hydrogel and hydrogel contact lenses tend to have relatively hydrophobic, non-wettable surfaces.

Those skilled in the art have recognized the need for modifying the surface of contact lenses so that they are compatible with the eye. It is known that increased hydrophilicity of a contact-lens surface improves the wettability of the contact lenses. This, in turn, is associated with improved wear comfort of the contact lens. Additionally, the surface chemistry of the lens can affect the lens's susceptibility to deposition, particularly the deposition of proteins and lipids from the tear fluid during lens wear. Accumulated deposition can cause eye discomfort or even inflammation. In the case of extended-wear lenses, the surface is especially important, since extended-wear lenses must be designed for high standards of comfort over an extended period of time, without requiring daily removal of the lenses before sleep. Thus, the regimen for the use of extended-wear lenses would not provide a daily period of time for the eye to rest or recover from any discomfort or other possible adverse effects of lens wear during the day. Accordingly, it is highly desirable that contact lenses be as comfortable as possible for wearers.

Various patents disclose the attachment of hydrophilic or otherwise biocompatible polymeric chains to the surface of a contact lens in order to render the lens more biocompatible. For example, U.S. Pat. No. 5,652,014 discloses amination of a substrate followed by reaction with other polymers, such as a polyethylene oxide star molecule or a sulfated polysaccharide. One problem with such an approach is that the polymer chain density is limited due to the difficult of attaching the polymer to the silicone substrate.

U.S. Pat. No. 5,344,701 discloses the attachment of oxazolinone or azlactone monomers to a substrate by means of plasma. The invention has utility in the field of surface-mediated or catalyzed reactions for synthesis or site-specific separations, including affinity separation of biomolecules, diagnostic supports and enzyme membrane reactors. The oxazolinone group is attached to a porous substrate apparently by reaction of the ethylenic unsaturation in the oxazolinone monomer with radicals formed by plasma on the substrate surface. Alternatively, the substrate can be coated with monomers and reacted with plasma to form a cross-linked coating. The oxazolinone groups that have been attached to the surface can then be used to attach a biologically active material, for example, proteins, since the oxazolinone is attacked by amines, thiols, and alcohols.

U.S. Pat. Nos. 5,352,714 and 5,364,918 disclose the use of oxazolinone monomers as internal wetting agents for contact lenses, which agents may migrate to the surface of the contact lens.

U.S. Pat. No. 5,804,318 discloses lubricious coatings for reducing the coefficients of friction of surfaces on medical devices, including hydrophilic copolymers containing some monomers having pendant tertiary amine functionality. The hydrogel coatings are covalently bondable to epoxy functionalized surfaces on the medical equipment.

It would be desirable to provide improved biomedical devices having an optically clear, hydrophilic coating on the surface thereof that renders the device more biocompatible. It would also be desirable to form a coating for a biomedical device such as a contact lens that is lubricious, highly wettable and more comfortable to wear for a longer period of time. In addition, it would be desirable to provide a coating with these properties that can be readily renewed to restore its properties to an as-new state.

SUMMARY OF THE INVENTION

In accordance with one embodiment of the present invention, a biomedical device including a hydrophilic surface is provided comprising: (a) a biomedical device obtained from a polymerization product of a monomeric mixture comprising (i) a polymerizable monomer containing a boronic acid moiety and an electron withdrawing moiety; and (ii) a biomedical device-forming comonomer; and (b) a hydrophilic reactive polymer having complementary reactive functionalities along the polymer chain, wherein the complementary reactive functionalities along the polymer chain of the hydrophilic reactive polymer of (b) binds with the boronic acid moieties of the biomedical device of (a), thereby producing a biocompatible coating which can be removed and re-applied to restore the surface properties of the biomedical device to substantially as-new condition.

In accordance with a second embodiment of the present invention, a method for treating a surface of a biomedical device is provided comprising: (a) providing a biomedical device obtained from a polymerization product of a monomeric mixture comprising (i) a polymerizable monomer containing a boronic acid moiety and an electron withdrawing moiety; and (ii) a biomedical device-forming comonomer; (b) providing a hydrophilic reactive polymer having complementary reactive functionalities along the polymer chain, (c) binding the complementary reactive functionalities along the polymer chain of the hydrophilic reactive polymer of (b) with the boronic acid moieties of the biomedical device of (a), thus forming a biocompatible coating on the surface of the medical device; (d) removing the biocompatible coating of step (c); and (e) repeating steps (b) and (c) to form a renewed biocompatible coating on the surface of the biomedical device having properties similar to the original biocompatible coating of step (c).

By treating the surface of the biomedical device having boronic acid moieties thereon with a hydrophilic reactive polymer having complementary reactive functionalities along the polymer chain such as, for example, a diol, which are capable of binding to the boronic acid moieties of the biomedical device, a highly wettable and/or lubricious surface on the biomedical device is advantageously achieved as compared to a non-treated biomedical device. As the biomedical device, such as a contact lens is worn over time, the hydrophilic reactive polymer having complementary reactive functionalities along the polymer chain will be removed from the contact lens due to, for example, tear film flow and blinking, thus exposing the surface of the lens to eye tissue and tear film. Thus, by further treating the surface of the lens with the same or different hydrophilic reactive polymer having complementary reactive functionalities which are capable of binding to the boronic acid moieties of the biomedical device, a renewed biocompatible coating on the surface of the biomedical device is achieved having properties similar to the original biocompatible coating. Accordingly, the lens remains more wettable and/or more lubricious, and therefore more comfortable to wear.

DETAILED DESCRIPTION OF THE PREFERRED EMBODIMENTS

The present invention is directed to the surface treatment of biomedical devices intended for direct contact with body tissue or body fluid including a method of modifying the surface of a contact lens to increase its hydrophilicity or wettability and lubriciousness. The surface treatment comprises binding complementary reactive functionalities along the polymer chain of a hydrophilic reactive polymer to the surface of the biomedical device by way of boronic acid reactive functionalities. As used herein the terms "bound", "binding", or terms of similar import, refer to various chemical interactions such as, electrostatic, ionic, complexation, hydrogen bond or other interaction between the hydrophilic reactive polymer and at least the boronic acid reactive functionalities at the surface of the device which results in the association of the coating composition with the device. Subsequently, the hydrophilic polymer chains will be removed from the device and then re-applied to achieve substantially as-new surface quality. As used herein, the term "as-new surface quality" means a re-applied surface resembling the original surface coating in appearance and material properties.

The term "biomedical device" as used herein shall be understood to mean any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye such as, for example, intraocular devices and contact lenses. The preferred biomedical devices are ophthalmic devices, particularly contact lenses, and most particularly contact lenses made from silicone hydrogels.

As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens, soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking. The present invention is especially advantageous for application to contact lenses, such as hydrogels, silicone hydrogels, and rigid-gas-permeable lens materials.

The biomedical devices of the present invention are formed from a polymerization product of (a) a polymerizable monomer containing a boronic acid moiety and an electron withdrawing moiety; and (b) a biomedical device-forming comonomer. Suitable polymerizable monomers containing a boronic acid moiety and an electron withdrawing moiety for use in forming the biomedical devices of the present invention include boronic acid-containing monomers having an electron withdrawing moiety and one or more polymerizable ethylenically unsaturated-containing radicals attached thereto. Representative examples of a "polymerizable ethylenically unsaturated-containing radical" include, by way of example, (meth)acrylate-containing radicals, (meth)acrylamido-containing radicals, vinylcarbonate-containing radicals, vinylcarbamate-containing radicals, styrene-containing radicals, itaconate-containing radicals, vinyl-containing radicals, vinyloxy-containing radicals, fumarate-containing radicals, maleimide-containing radicals, vinylsulfonyl radicals and the like. As used herein, the term "(meth)" denotes an optional methyl substituent. Thus, for example, terms such as "(meth)acrylate" denotes either methacrylate or acrylate, and "(meth)acrylamide" denotes either methacrylamide or acrylamide.

In one embodiment, a polymerizable ethylenically unsaturated radical can be represented by the general formula:

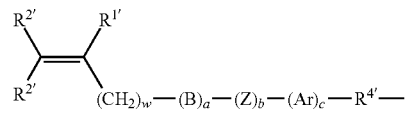

wherein $R^{1'}$ is hydrogen or a alkyl group having 1 to 6 carbon atoms such as methyl; each $R^{2'}$ is independently hydrogen, an alkyl radical having 1 to 6 carbon atoms, or a —CO—Y—$R^{5'}$ radical wherein Y is —O—, —S— or —NH— and $R^5$ is an alkyl radical having 1 to about 10 carbon atoms; $R^{4'}$ is a linking group (e.g., a divalent alkenyl radical having 1 to about 12 carbon atoms); B denotes —O— or —NH—; Z denotes —CO—, —OCO— or —COO—; Ar denotes an aromatic radical having 6 to about 30 carbon atoms; w is 0 to 6; a is 0 or 1; b is 0 or 1; and c is 0 or 1. The polymerizable ethylenically unsaturated-containing radicals can be attached to the boronic acid-containing monomers having an electron withdrawing moiety as pendent groups, terminal groups or both.

As used herein, the term "electron withdrawing moiety" refers to a group which has a greater electron withdrawing effect than hydrogen. A variety of electron-withdrawing moieties are known and include, by way of example, halogens (e.g., fluoro, chloro, bromo, and iodo groups), $NO_2$, $NR_3^+$, CN, COOH(R), $CF_3$, and the like. The pH of the boronic acid-containing monomer can be adjusted by placing the electron withdrawing moiety in, e.g., a position meta to the boronic acid moiety on the phenyl ring.

Representative examples of suitable polymerizable monomers containing a boronic acid moiety and an electron withdrawing moiety include polymerizable ethylenically unsaturated alkyl boronic acids having an electron withdrawing moiety; polymerizable ethylenically unsaturated cycloalkyl boronic acids having an electron withdrawing moiety; polymerizable ethylenically unsaturated aryl boronic acids having an electron withdrawing moiety and the like and mixtures thereof. Preferred boronic acid polymerizable monomers are derived from 3-vinylphenylboronic acid or 3-methacrylamidophenylboronic acid.

Representative examples of alkyl groups for use herein include, by way of example, a straight or branched hydrocarbon chain radical containing carbon and hydrogen atoms of from 1 to about 18 carbon atoms with or without unsaturation, to the rest of the molecule, e.g., methyl, ethyl, n-propyl, 1-methylethyl (isopropyl), n-butyl, n-pentyl, etc., and the like.

Representative examples of cycloalkyl groups for use herein include, by way of example, a substituted or unsubstituted non-aromatic mono or multicyclic ring system of about 3 to about 24 carbon atoms such as, for example, cyclopropyl, cyclobutyl, cyclopentyl, cyclohexyl, perhydronapthyl, adamantyl and norbornyl groups bridged cyclic group or spriro-bicyclic groups, e.g., sprio-(4,4)-non-2-yl and the like, optionally containing one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

In one embodiment, a polymerizable monomer containing a boronic acid moiety and an electron withdrawing moiety is represented by the general formula:

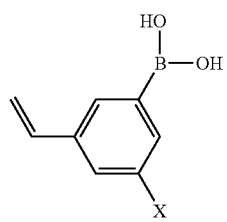

wherein X is an electron withdrawing group such as $CF_3$, $-NO_2$, $-F$, $-Cl$ or $-Br$.

The polymerizable monomers containing a boronic acid moiety and an electron withdrawing moiety can be prepared by the general reaction sequences set forth in Schemes I and II below:

SCHEME I

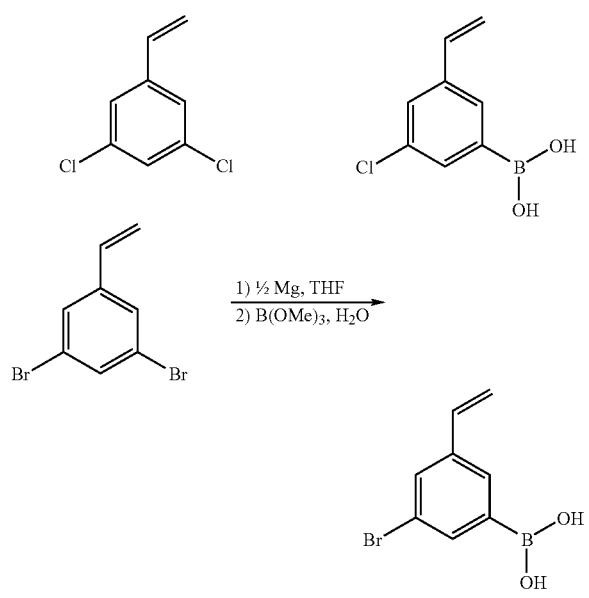

SCHEME II

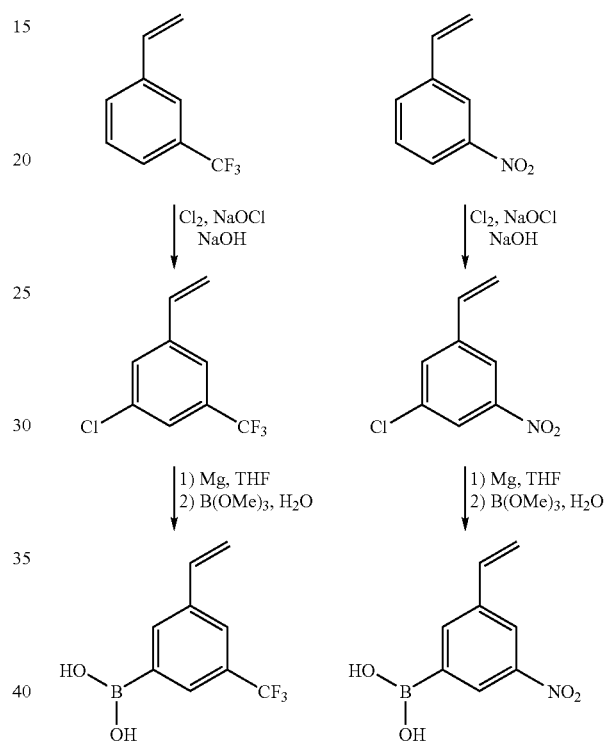

In addition to the polymerizable monomer containing a boronic acid moiety and an electron withdrawing moiety, the monomeric mixture will further contain one or more biomedical device-forming comonomers. Generally, the biomedical device-forming comonomer contains at least one polymerizable group. In one embodiment, the biomedical device-forming comonomer is an ophthalmic device-forming comonomer such as a contact lens-forming comonomer. In another embodiment, the biomedical device-forming comonomer is a hydrogel lens forming-containing monomer. Hydrogels comprise a hydrated, cross-linked polymeric system containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer.

Either the silicone-containing monomer or the hydrophilic monomer may function as a crosslinking agent (a crosslinking agent being defined as a monomer having multiple polymerizable functionalities), or alternately, a separate crosslinking agent may be employed in the initial monomer mixture from which the hydrogel copolymer is formed. (As used herein, the term "monomer" or "monomeric" and like terms denote relatively low molecular weight compounds that are polymerizable by free radical polymerization, as well as higher molecular weight compounds also referred to as "prepolymers", "macromonomers", and related terms.) Silicone hydrogels typically have a water content between about 10 to about 80 weight percent.

Applicable silicone-containing monomers for use in the formation of contact lenses such as silicone hydrogels are well known in the art and numerous examples are provided in, for example, U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth)acrylic monomer is represented by the structure of Formula I:

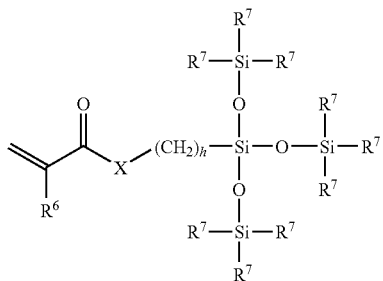

(I)

wherein X denotes —O— or —NR— wherein R denotes hydrogen or a $C_1$-$C_4$ alkyl; each $R^6$ independently denotes hydrogen or methyl; each $R^7$ independently denotes a lower alkyl radical, phenyl radical or a group represented by

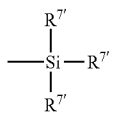

wherein each $R^{7'}$ independently denotes a lower alkyl or phenyl radical; and h is 1 to 10.

Representative examples of other applicable silicon-containing monomers includes, but are not limited to, bulky polysiloxanylalkyl carbamate monomers as generally depicted in Formula Ia:

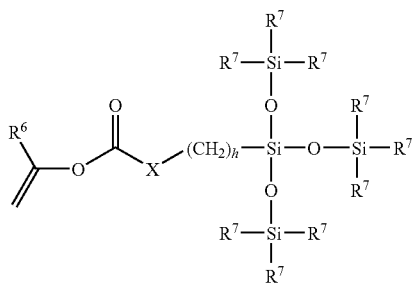

(Ia)

wherein X denotes —NR—; wherein R denotes hydrogen or a $C_1$-$C_4$ alkyl; $R^6$ denotes hydrogen or methyl; each $R^7$ independently denotes a lower alkyl radical, phenyl radical or a group represented by

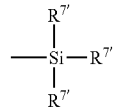

wherein each $R^{7'}$ independently denotes a lower alkyl or phenyl radical; and h is 1 to 10, and the like.

Examples of bulky monomers are 3-methacryloyloxypropyltris(trimethyl-siloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyldisiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris (trimethylsiloxy)silyl]propyl allyl carbamate; 3-[tris (trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety or publications, including Lai, Yu-Chin, "The Role of Bulky Polysiloxanylalkyl Methacryates in Polyurethane-Polysiloxane Hydrogels," *Journal of Applied Polymer Science*, Vol. 60, 1193-1199 (1996). PCT Published Application No. WO 96/31792 also discloses examples of such monomers, the contents of which are hereby incorporated by reference in its entirety. Further examples of silicone urethane monomers are represented by Formulae II and III:

$$E(*D*A*D*G)_a*D*A*D*E'; \text{ or} \quad (II)$$

$$E(*D*G*D*A)_a*D*A*D*E'; \text{ or} \quad (III)$$

wherein:

D denotes an alkyl diradical, an alkyl cycloalkyl diradical, a cycloalkyl diradical, an aryl diradical or an alkylaryl diradical having 6 to about 30 carbon atoms;

G denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A denotes a divalent polymeric radical of Formula IV:

$$\text{—(CH}_2)_{m'}\left[\begin{array}{c}R^s\\|\\\text{Si}\\|\\R^s\end{array}\text{—O—}\begin{array}{c}R^s\\|\\\text{Si}\\|\\R^s\end{array}\right]_p\text{(CH}_2)_{m'}\text{—} \quad \text{(IV)}$$

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula V:

$$\begin{array}{c}R^8\\R^9\diagdown\diagup\\ \diagup\diagdown\\R^9\end{array}\text{(CH}_2)_w\text{—(X)}_x\text{—(Z)}_z\text{—(Ar)}_y\text{—R}^{10}\text{—} \quad \text{(V)}$$

wherein: $R^8$ is hydrogen or methyl;

$R^9$ is independently hydrogen, an alkyl radical having 1 to 6 carbon atoms, or a —CO—Y—$R^{11}$ radical wherein Y is —O—, —S— or —NH—;

$R^{10}$ is a divalent alkylene radical having 1 to about 10 carbon atoms;

$R^{11}$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

A preferred silicone-containing urethane monomer is represented by Formula VI:

$$\begin{array}{c}CH_3\\|\\\diagup\diagdown\\\diagdown\diagup\\|\\O\end{array}\text{O}\diagdown\text{CH}_2\text{—}$$

Another class of representative silicone-containing monomers includes fluorinated monomers. Such monomers have been used in the formation of fluorosilicone hydrogels to reduce the accumulation of deposits on contact lenses made therefrom, as described in, for example, U.S. Pat. Nos. 4,954,587; 5,010,141 and 5,079,319. The use of silicone-containing monomers having certain fluorinated side groups, i.e., —($CF_2$)—H, have been found to improve compatibility between the hydrophilic and silicone-containing monomeric units, see, e.g., U.S. Pat. Nos. 5,321,108 and 5,387,662.

The above silicone materials are merely exemplary, and other materials for use in forming biomedical devices according to the present invention and have been disclosed in various publications and are being continuously developed for use in contact lenses and other biomedical devices can also be used. For example, a biomedical device-forming comonomer can be a cationic monomer such as cationic silicone-containing monomer or cationic fluorinated silicone-containing monomers.

The monomer mixtures can also contain one or more hydrophilic monomers. Suitable hydrophilic monomers include one or more unsaturated carboxylic acids, vinyl lactams, amides, polymerizable amines, vinyl carbonates, vinyl carbamates, oxazolone monomers, and the like and mixtures thereof. Useful unsaturated carboxylic acids include methacrylic acid or acrylic acid. Useful amides include acrylamides such as N,N-dimethylacrylamide and N,N-dimethylmethacrylamide. Useful vinyl lactams include cyclic lactams such as N-vinyl-2-pyrrolidone. Examples of other hydrophilic monomers include poly(alkene glycols) functionalized with polymerizable groups, glyceryl methacrylate, and N-vinyl-N-methylacetamide. Examples of useful functionalized poly(alkene glycols) include poly(diethylene glycols) of varying chain length containing monomethacrylate or dimethacrylate end caps. In a preferred embodiment, the poly(alkene glycol) polymer contains at least two alkene glycol monomeric units. Still further examples are the hydrophilic $$\text{E''}\left[\begin{array}{c}O\\||\\\text{OCN}\\|\\H\end{array}\text{—R}^{12}\text{—}\begin{array}{c}O\\||\\\text{NCOCH}_2\text{CH}_2\text{OCH}_2\text{CH}_2\text{OCN}\\|\\H\end{array}\text{—R}^{12}\text{—}\begin{array}{c}O\\||\\\text{NCO(CH}_2)_m\\|\\H\end{array}\left(\begin{array}{c}CH_3\\|\\\text{Si—O}\\|\\CH_3\end{array}\right)_p\begin{array}{c}CH_3\\|\\\text{Si—(CH}_2)_m\\|\\CH_3\end{array}\right]_a \quad \text{(VI)}$$

$$\text{E''}\text{—}\begin{array}{c}H\\|\\\text{OCN}\\||\\O\end{array}\text{—R}^{12}\text{—}\begin{array}{c}H\\|\\\text{NCOCH}_2\text{CH}_2\text{OCH}_2\text{CH}_2\text{OCN}\\||\\O\end{array}\text{—R}^{12}\text{—}\begin{array}{c}H\\|\\\text{NCO}\\||\\O\end{array}$$

wherein m is at least 1 and is preferably 3 or 4, a is at least 1 and preferably is 1, p is a number which provides a moiety weight of about 400 to about 10,000 and is preferably at least about 30, $R^{12}$ is a diradical of a diisocyanate after removal of the isocyanate group, such as the diradical of isophorone diisocyanate, and each E'' is a group represented by:

vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. The hydrophilic monomers can be present in the monomeric mixtures in an amount ranging from 0 to about 70 weight percent, based on the total weight of the mixture.

The monomer mixtures can also contain one or more hydrophobic monomers. Suitable hydrophobic monomers include $C_1$-$C_{20}$ alkyl and $C_3$-$C_{20}$ cycloalkyl(meth)acrylates, substituted and unsubstituted $C_6$-$C_{30}$ aryl(meth)acrylates, (meth)acrylonitriles, fluorinated alkyl methacrylates, long-chain acrylamides such as octyl acrylamide, and the like. The hydrophobic monomers can be present in the monomeric mixtures in an amount ranging from 0 to about 30 weight percent, based on the total weight of the mixture.

The monomer mixtures can also contain one or more crosslinking monomers. The crosslinking monomer may be a material having multiple polymerizable functionalities, preferably vinyl functionalities. Representative examples of crosslinking monomers include divinylbenzene; allyl methacrylate; ethyleneglycol di(meth)acrylate, tetraethyleneglycol di(meth)acrylate, polyethyleneglycol di(meth)acrylate; vinylcarbonate derivatives of the glycol di(meth)acrylates and the like. The crosslinking monomers can be present in the monomeric mixtures in an amount ranging from 0 to about 40 weight percent, based on the total weight of the mixture.

In order to prepare the biomedical devices of the present invention that are capable of complexation with the hydrophilic coating polymer, it is necessary that the boronic acid groups are present at the surface of the device and are capable of forming complexes with suitable hydrophilic coating polymers at physiological pH (e.g. a pH of about 6.8 to about 7.6). Concentration of the boronic acid groups at the surface of the biomedical device can be accomplished by providing a mold surface that is capable of complexation with boronic acid groups. A mold surface having any of the following functional groups are capable of complexation with boronic acid groups: 1,2 diols, 1,3 diols, dicarboxylic acids, α-hydroxy carboxylic acids and the like. Representative examples of suitable mold materials are ethyl vinyl alcohol resin, poly(ethylene-co-vinyl alcohol), air-plasma oxidized polypropylene and the like.

To meet the pKa requirement, boronic acid groups such as aryl boronic acids are commonly copolymerized with tertiary amines so that some of the amine groups are placed adjacent to the boronic acid groups to interact with the boronic acid groups and lower the effective pKa of the boronic acid to the about 6.8 to about 7.6 range. However, the addition of a polymerizable tertiary amine to a contact lens formulation at a low concentration is generally not desirable because the probability of forming boronic acid—tertiary amine dimer sequences is relatively low. The present invention advantageously employs boronic acid monomers having an electron withdrawing substituent to obviate the need to incorporate a tertiary amine into, for example, a lens formulation, while being able to meet the pKa requirement and allow the boronic acid groups to be present at the surface of the lens.

If desired, the monomer mixtures can also contain a monomer having a tertiary-amine moiety such that the boronic acid moieties on the surface of the biomedical device are physiologically acceptable, i.e., a pH value of about 6.8 to about 7.6 (physiological pH values). Examples of monomers copolymerizable with the boronic acid monomer are ethylenically unsaturated monomers containing the tertiary-amine moiety. Specific examples include: 2-(N,N-dimethyl)ethylamino (meth)acrylate, N-[2-(dimethylamino)ethyl](meth)acrylamide, N-[(3-dimethylamino)propyl] (meth)acrylate, N-[3-dimethylamino)propyl](meth)acrylamide and vinylbenzyl-N,N-dimethylamine.

The biomedical devices of the present invention, e.g., contact lenses or intraocular lenses, can be prepared by polymerizing the foregoing monomeric mixtures to form a product that can be subsequently formed into the appropriate shape by, for example, lathing, injection molding, compression molding, cutting and the like. For example, in producing contact lenses, the initial monomeric mixture may be polymerized in tubes to provide rod-shaped articles, which are then cut into buttons. The buttons may then be lathed into contact lenses.

Alternately, the contact lenses may be cast directly in molds, e.g., polypropylene molds, from the monomeric mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the monomer mixture to a mold, and spinning the mold in a controlled manner while exposing the monomer mixture to a radiation source such as UV light. Static casting methods involve charging the monomeric mixture between two mold sections, one mold section shaped to form the anterior lens surface and the other mold section shaped to form the posterior lens surface, and curing the monomeric mixture while retained in the mold assembly to form a lens, for example, by free radical polymerization of the monomeric mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetal peroxide, lauroyl peroxide, decanoyl peroxide, stearoyl peroxide, benzoyl peroxide, tertiarylbutyl peroxypivalate, peroxydicarbonate, and the like. Representative UV initiators are those known in the art and include benzoin methyl ether, benzoin ethyl ether, Darocure 1173, 1164, 2273, 1116, 2959, 3331 (EM Industries) and Igracure 651 and 184 (Ciba-Geigy), and the like. Generally, the initiator will be employed in the monomeric mixture at a concentration of about 0.01 to 1 percent by weight of the total mixture.

Polymerization of the mixtures will yield a polymer, that when hydrated, forms a hydrogel. Generally, the mixture will contain the polymerizable monomer having one or more boronic acid moieties in an amount ranging from about 0.1 to about 10 weight percent, and preferably from about 0.5 to about 2 weight percent, based on the total weight of the mixture, and the biomedical device-forming comonomer in an amount ranging from about 5 to about 90 weight percent and preferably from about 20 to about 60 weight percent, based on the total weight of the mixture.

When producing a hydrogel lens, the mixture may further include at least a diluent that is ultimately replaced with water when the polymerization product is hydrated to form a hydrogel. Generally, the water content of the hydrogel is greater than about 5 weight percent and more commonly between about 10 to about 80 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof.

As previously stated, the biomedical devices of the present invention, such as a contact lens, should have a sufficient amount of concentrated boronic acid on the surface to provide enhanced wettability and/or lubriciousness to the lens. One manner to accomplish this is to cast the monomer mix in an appropriate mold resin such as an ethyl vinyl alcohol resin and then wet release of the lens from the mold. Another manner is to incorporate the boronic acid-containing monomer into a surface active monomer, see, e.g., U.S. Pat. Nos. 5,117,165 and 5,219,965.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

The biomedical devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

As indicated above, the present invention is directed to the modification of the surface of the biomedical device such as a contact lens by means of removably attaching the surface hydrophilic polymer chains. The term "removably attaching" refers to creating a chemical bond between the substrate material and the hydrophilic polymer chains which can be severed without substantial mechanical damage to the substrate. For example, as the contact lens is worn over time, the hydrophilic reactive polymer can be gradually removed from the contact lens, due to tear film flow and blinking or desorption attributable to substances in the tear film such as mucin that can also complex with boronic acid moieties.

In one embodiment, the hydrophilic reactive polymer can be monomeric units containing 1,2- or 1,3-diols along the backbone of the polymer chain, as such materials complex well with the boronic acid moieties on the surface of the device. In one embodiment, examples of hydrophilic reactive polymer include diol-terminated polymeric materials such as diol-terminated polyvinyl pyrrolidinone (PVP); diol-terminated polyacrylamides; diol-terminated polyethylene oxides; diol-terminated polyethylene oxide (PEO)/polypropylene oxide (PPO) block copolymers such as functionalized Pluronics® and reverse Pluronics® (BASF Wyandotte Corp., Wyandotte, Mich.) and the like and mixtures thereof. In one embodiment, the hydrophilic reactive polymer is a poly(vinyl alcohol).

In another embodiment, the hydrophilic reactive polymers can be copolymers derived from the polymerization product of ethylenically unsaturated epoxy-containing monomers, such as glycidyl methacrylate, vinylcyclohexyl-1,2-epoxide or glycidyl vinyl carbonate, in which the epoxy group is then hydrolyzed to provide a copolymer units containing 1,2- or 1,3-diols along the backbone of the polymer chain. Such hydrophilic reactive polymers are produced through free radical polymerization techniques known to those skilled in the art.

Generally, the hydrophilic reactive polymers comprise about 1 to about 100 mole percent of reactive monomeric units, more preferably about 5 to about 50 mole percent, most preferably about 10 to about 40 mole percent. The polymers may comprise 0 to about 99 mole percent of non-reactive hydrophilic monomeric units, preferably about 50 to about 95 mole percent, more preferably about 60 to about 90 mole percent (the reactive monomers, once reacted may also be hydrophilic, but are by definition mutually exclusive with the monomers referred to as hydrophilic monomers which are non-reactive). The weight average molecular weight of the hydrophilic reactive polymer may suitably range from about 200 to about 1,000,000, preferably from about 1,000 to about 500,000, and most preferably from about 5,000 to about 100,000.

Suitable hydrophilic non-reactive monomers include aprotic types or protic types or mixtures thereof. Suitable aprotic types include acrylamides such as N,N-dimethylacrylamide, N,N-dimethylmethacrylamide, N-methylmethacrylamide, N-methylacrylamide and the like, but preferably N,N-dimethylacrylamide for increased hydrophilicity; lactams such as N-vinylpyrrolidinone and the like, poly(alkylene oxides) such as methoxypolyoxyethylene methacrylates and the like and mixtures thereof. Suitable protic types include methacrylic acid, hydroxyalkyl(meth)acrylates such as 2-hydroxyethyl methacrylate and the like and mixtures thereof.

If desired, the copolymers may include monomeric units which are hydrophobic optionally may be used in amounts up to 35 mole percent, preferably 0 to 20 mole percent, most preferably 0 to 10 mole percent. Examples of hydrophobic monomers are alkyl methacrylate, fluorinated alkyl methacrylates, long-chain acrylamides such as octyl acrylamide, and the like.

In another embodiment, the hydrophilic reactive polymers can be polymers derived from the polymerization product of an ethylenically unsaturated alkanolamines. Suitable ethylenically unsaturated-containing alkanolamines include those of the general formula $R^{13}$—$N(R^{14}OH)_2$ wherein $R^{13}$ is an ethylenically unsaturated-containing radical as defined herein above; and $R^{14}$ is independently an alkylene group having from one to about six carbon atoms. Suitable ethylenically unsaturated-containing alkanolamines include, but are not limited to, ethylenically unsaturated-containing diethanolamine, ethylenically unsaturated-containing dipropanolamine, ethylenically unsaturated-containing di-isopropanolamine, and the like and mixtures thereof.

In another embodiment, the hydrophilic reactive polymers can be a carboxylic acid-containing polymer or copolymer. Suitable carboxylic acid-containing polymers include, but are not limited to, poly(acrylic acid), poly(methacrylic acid), poly(hyaluronic acid) and the like and mixtures thereof. Suitable carboxylic acid-containing copolymers include, but are not limited to, poly(vinylpyrrolidinone(VP)-co-acrylic acid (AA)), poly(methylvinylether-alt-maleic acid), poly(acrylic acid-graft-ethylene oxide), poly(acrylic acid-co-methacrylic acid), poly(acrylamide-co-AA), poly(AA-co-maleic acid), poly(butadiene-maleic acid) and the like.

In another embodiment, the hydrophilic reactive polymers can be a polyol. Useful polyols include those polyols containing 2 to about 12 carbon atoms and preferably 2 to 4 carbon atoms and from 2 to 8 hydroxyl groups. Representative examples of polyols for use herein include glycerin, ethylene glycol, poly(ethylene glycol), propylene glycol, sorbitol, mannitol, cellulose-containing polymers, monosaccharides, disaccharides, and neutral oligo-polysaccharides, such as from methylcellulose, hydroxypropylmethylcellulose, hydroxypropylguar, and oligomers of poly(vinyl alcohol) and derivatives thereof.

In another embodiment, the hydrophilic reactive polymers can contain ring-opening monomeric units. In one embodiment of the present invention, the ring-opening monomeric units are derived from a ring-opening reactive monomer having an azlactone group represented by the following formula:

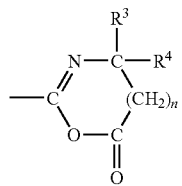

wherein $R^3$ and $R^4$ are independently an alkyl group having 1 to 14 carbon atoms, a cycloalkyl group having 3 to about 14 carbon atoms, an aryl group having 5 to about 12 ring atoms, an arenyl group having 6 to about 26 carbon atoms, and 0 to 3 heteroatoms non-peroxidic selected from S, N, and O, or $R^3$ and $R^4$ taken together with the carbon to which they are joined can form a carbocyclic ring containing 4 to 12 ring atoms, and n is an integer 0 or 1. Such monomeric units are disclosed in U.S. Pat. No. 5,177,165.

The ring structure of such reactive functionalities is susceptible to nucleophilic ring-opening reactions with complementary reactive functional groups on the surface of substrate being treated. For example, the azlactone functionality can react with primary amines, hydroxyl radicals or the like which may be present on the surface of the device to form a covalent bond between the substrate and the hydrophilic reactive polymer at one or more locations along the polymer. A plurality of attachments can form a series of polymer loops on the substrate, wherein each loop comprises a hydrophilic chain attached at both ends to the substrate.

Azlactone-functional monomers for making the hydrophilic reactive polymer can be any monomer, prepolymer, or oligomer comprising an azlactone functionality of the above formula in combination with a vinylic group on an unsaturated hydrocarbon to which the azlactone is attached. Preferably, azlactone-functionality is provided in the hydrophilic polymer by 2-alkenyl azlactone monomers. The 2-alkenyl azlactone monomers are known compounds, their synthesis being described in, for example, U.S. Pat. Nos. 4,304,705; 5,081,197; and 5,091,489, the content of which are incorporated by reference herein. Suitable 2-alkenyl azlactones include, but are not limited to, 2-ethenyl-1,3-oxazolin-5-one, 2-ethenyl-4-methyl-1,3-oxazolin-5-one, 2-isopropenyl-1,3-oxazolin-5-one, 2-isopropenyl-4-methyl-1,3-oxazolin-5-one, 2-ethenyl-4,4-dimethyl-1,3-oxazolin-5-one, 2-isopropenyl-4,-dimethyl-1,3-oxazolin-5-one, 2-ethenyl-4-methylethyl-1,3-oxazolin-5-one, 2-isopropenyl-4-methyl-4-butyl-1,3-oxazolin-5-one, 2-ethenyl-4,4-dibutyl-1,3-oxazolin-5-one, 2-isopropenyl-4-methyl-4-dodecyl-1,3-oxazolin-5-one, 2-isopropenyl-4,4-diphenyl-1,3-oxazolin-5-one, 2-isopropenyl-4,4-pentamethylene-1,3-oxazolin-5-one, 2-isopropenyl-4,4-tetramethylene-1,3-oxazolin-5-one, 2-ethenyl-4,4-diethyl-1,3-oxazolin-5-one, 2-ethenyl-4-methyl-4-nonyl-1,3-oxazolin-5-one, 2-isopropenyl-methyl-4-phenyl-1,3-oxazolin-5-one, 2-isopropenyl-4-methyl-4-benzyl-1,3-oxazolin-5-one, and 2-ethenyl-4,4-pentamethylene-1,3-oxazolin-5-one. In a preferred embodiment, the azlactone monomers are represented by the following general formula:

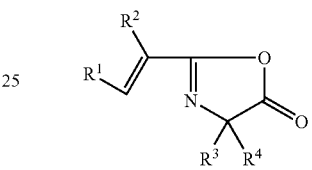

where $R^1$ and $R^2$ independently denote a hydrogen atom or a lower alkyl radical with one to six carbon atoms, and $R^3$ and $R^4$ independently denote alkyl radicals with one to six carbon atoms or a cycloalkyl radical with five or six carbon atoms. Specific examples include 2-isopropenyl-4,4-dimethyl-2-oxazolin-5-one (IPDMO), 2-vinyl-4,4-dimethyl-2-oxazolin-5-one (VDMO), spiro-4'-(2'-isopropenyl-2'-oxazolin-5-one) cyclohexane (IPCO), cyclohexane-spiro-4'-(2'-vinyl-2'-oxazol-5'-one) (VCO), and 2-(4-propenyl)-4,4-dimethyl-oxazol-5-one (PDMO) and the like. These compounds and their preparation are known in the art, see, e.g., U.S. Pat. No. 6,858,310, the contents of which are incorporated by reference herein.

The azlactone-functional monomers can be copolymerized with hydrophilic and/or hydrophobic comonomers to form hydrophilic reactive polymers. Representative examples of comonomers that can be copolymerized with azlactone functional moieties to form the hydrophilic reactive polymers used to coat a biomedical device include those mentioned above, such as dimethylacrylamide (DMA), hydroxyethyl methacrylate (HEMA), and/or N-vinylpyrrolidone (NVP). Other examples of such comonomers are disclosed in European Patent Publication 0 392 735, the disclosure of which is incorporated by reference. In a preferred embodiment, the hydrophilic reactive polymer is derived from VDMO and DMA is used as a comonomer in order to impart hydrophilicity to the copolymer.

The azlactone-functional monomers can be copolymerized with other monomers in various combinations of weight percentages. Using a monomer of similar reactivity ratio to that of an azlactone monomer will result in a random copolymer. Determination of reactivity ratios for copolymerization are disclosed in Odian, *Principles of Polymerization,* 2nd Ed., John Wiley & Sons, p. 425-430 (1981), the disclosure of which is incorporated by reference herein. Alternatively, use of a comonomer having a higher reactivity to that of an azlactone will tend to result in a block copolymer chain with a higher concentration of azlactone-functionality near the terminus of the chain.

Although not as preferred as monomers, azlactone-functional prepolymers or oligomers having at least one free-radically polymerizable site can also be utilized for providing azlactone-functionality in the hydrophilic reactive polymer according to the present invention. Azlactone-functional oligomers, for example, are prepared by free radical polymerization of azlactone monomers, optionally with comonomers as described in U.S. Pat. Nos. 4,378,411 and 4,695,608, incorporated by reference herein. Representative examples of azlactone-functional oligomers and prepolymers are disclosed in U.S. Pat. Nos. 4,485,236 and 5,081,197 and European Patent Publication 0 392 735, the contents of which are incorporated by reference herein.

The hydrophilic polymer chains are attached to the surface by means of exposing the surface of the biomedical device to the hydrophilic reactive polymer (inclusive of oligomers) having reactive functionalities which attach to at least the boronic acid reactive groups on the surface of the biomedical device. In other words, chemical functionality at the surface of the biomedical device is utilized to covalently attach the hydrophilic polymers to the device. For example, the hydrophilic reactive polymers can have alcohol reactive functionality, i.e., a diol, that may then react with the boronic acid moieties on surface of the device. As one skilled in the art will readily appreciate, the hydrophilic polymer chains may be additionally attached to the surface of the device by means of exposing the surface to hydrophilic reactive polymers (inclusive of oligomers) having (primary or secondary) amine groups complementary to azlactone reactive groups in the biomedical device-forming material or having carboxylic acid complementary groups complementary to epoxy reactive groups in the biomedical device-forming material.

The surface of the biomedical device can be treated by contacting the surface with an ophthalmic solution containing the hydrophilic reactive polymer. The solutions generally include compositions for direct instillation in the eye, including eye drop solutions and contact lens treating solutions distilled directly in the eye such as for rewetting a contact lens while worn as well as those that also qualify as a multi-purpose solution. Ophthalmic compositions also include compositions instilled indirectly in the eye, such as contact lens treating solutions for treating the contact lens prior to the lens being inserted on the eye or a packaging solution for storing the lens.

The ophthalmically acceptable solutions according to the present invention are physiologically compatible. Specifically, the compositions must be "ophthalmically safe" for use with a contact lens, meaning that a contact lens treated with the solution is generally suitable and safe for direct placement on the eye without rinsing, that is, the solution is safe and comfortable for daily contact with the eye via a contact lens that has been wetted with the solution. An ophthalmically safe composition has a tonicity and pH that is compatible with the eye and comprises materials, and amounts thereof, that are non-cytotoxic according to ISO (International Standards Organization) standards and U.S. FDA regulations. The compositions should be sterile in that the absence of microbial contaminants in the product prior to release must be statistically demonstrated to the degree necessary for such products.

In general, the hydrophilic reactive polymer disclosed herein can be present in the ophthalmic solution in an amount ranging from about 0.001 to about 10% w/w and preferably from about 0.1 to about 2% w/w. The ophthalmic solutions may be in the form of drops and are useful as a component of a contact lens cleaning, disinfecting or conditioning composition containing such materials. In one embodiment, the compositions and/or solutions of the present invention may be formulated as a "multi-purpose solution". A multi-purpose solution is useful for cleaning, disinfecting, storing, and rinsing a lens, particularly soft contact lenses. Multi-purpose solutions do not exclude the possibility that some wearers, for example, wearers particularly sensitive to chemical disinfectants or other chemical agents, may prefer to rinse or wet a contact lens with another solution, for example, a sterile saline solution prior to insertion of the lens. The term "multi-purpose solution" also does not exclude the possibility of periodic cleaners not used on a daily basis or supplemental cleaners for further removing proteins, for example, enzyme cleaners, which are typically used on a weekly basis. By the term "cleaning" is meant that the solution contains one or more agents in sufficient concentrations to loosen and remove loosely held lens deposits and other contaminants on the surface of a contact lens, which may be used in conjunction with digital manipulation (e.g., manual rubbing of the lens with a solution) or with an accessory device that agitates the solution in contact with the lens, for example, a mechanical cleaning aid.

Traditionally, multi-purpose solutions on the market have required a regimen involving mechanical rubbing of the lens with the multi-purpose solution, in order to provide the required disinfection and cleaning. Such a regimen is required under governmental regulatory authorities (e.g., the FDA or U.S. Food & Drug Administration (FDA)) for a Chemical Disinfection System that does not qualify as a Chemical Disinfecting Solution. In one embodiment of the present invention, it is possible to formulate a cleaning and disinfecting product that, on one hand, is able to provide improved cleaning and disinfection in the absence of a rubbing regimen and, on the other hand, is gentle enough to be used as a wetting agent, e.g. as an eye drop. For example, a product qualifying as a Chemical Disinfecting Solution must meet biocidal performance criteria established by the US FDA for Contact Lens Care Products (May 1, 1997) which criteria does not involve rubbing of the lenses. In one embodiment of the present invention, a composition is formulated to meet the requirements of the FDA or ISO Stand-Alone Procedure for contact lens disinfecting products. Similarly, the compositions of the present invention can be formulated to provide enhanced cleaning without the use of a rubbing regimen. Such formulations may ensure higher patient compliance and greater universal appeal than traditional multi-purpose disinfecting and cleaning products. A multi-purpose solution preferably has a viscosity of less than about 75 cps, preferably about 1 to about 50 cps, and most preferably about 1 to about 25 cps and is preferably at least about 95 percent weight by volume water in the total composition.

The aqueous ophthalmic solutions may contain, in addition to the hydrophilic reactive polymer described above, one or more antimicrobial agents, preservatives and the like. The compositions generally include a primary antimicrobial agent. Antimicrobial agents suitable for use in the present invention include chemicals that derive their antimicrobial activity through a chemical or physiochemical interaction with the microbial organisms. These agents may be used alone or in combination.

Suitable known ophthalmically acceptable antimicrobial agents include, but are not limited to, a biguanide or a salt or free base thereof, quaternary ammonium compound or a salt thereof or free base thereof; terpene or derivative thereof, a branched, glycerol monoalkyl ether, a branched, glycerol monoalkyl amine, a branched, glycerol monoalkyl sulphide, a fatty acid monoester, wherein the fatty acid monoester comprises an aliphatic fatty acid portion having six to fourteen carbon atoms, and an aliphatic hydroxyl portion, amidoamine compound, and the like and combinations thereof.

Suitable biguanide antimicrobial agents for use in the ophthalmic compositions can be any biguanide or salt thereof known in the art. Representative biguanides include non-polymeric biguanides, polymeric biguanides, salts thereof, free bases thereof and the like and mixtures thereof. Representative non-polymeric biguanides are the bis(biguanides), such as alexidine, chlorhexidine, salts of alexidine, e.g., alexidine HCl, salts of chlorhexidine, alexidine free base, and the like and mixtures thereof. The salts of alexidine and chlorhexidine can be either organic or inorganic and are typically disinfecting nitrates, acetates, phosphates, sulfates, halides and the like.

Representative polymeric biguanides include polymeric hexamethylene biguanides (PHMB) (commercially available from Zeneca, Wilmington, Del.), their polymers and water-soluble salts. In one embodiment, water-soluble polymeric biguanides for use herein can have a number average molecular weight of at least about 1,000 and more preferably a number average molecular weights from about 1,000 to about 50,000. Suitable water-soluble salts of the free bases include, but are not limited to, hydrochloride, borate, acetate, gluconate, sulfonate, tartrate and citrate salts. Generally, the hexamethylene biguanide polymers, also referred to as polyaminopropyl biguanide (PAPB), have number average molecular weights of up to about 100,000. Such compounds are known and are disclosed in U.S. Pat. No. 4,758,595 which patent is incorporated herein be reference.

PHMB is best described as a polymeric biguanide composition comprising at least three and preferably at least six biguanide polymers, which we refer to as PHMB-A, PHMB-CG and PHMB-CGA, the general chemical structures of which are depicted below.

major PHMB polymers above, the percentage of cyanoguardino end caps is also about 50% of the total number of terminal groups. In this application we refer to this conventional polymeric biguanide composition as poly(hexamethylene biguanide) or PHMB.

A new synthetic route to polymeric biguanide compositions is described in copending U.S. provisional application Ser. Nos. 60/853,579, filed Oct. 23, 2006, and 60/895,770, filed Mar. 20, 2007, the entire disclosure of each of which is incorporated by reference herein. The new synthetic route provides a polymeric biguanide composition comprising less than 18 mole % of terminal amine groups as measured by $^{13}$CNMR. The polymeric biguanide composition can also be characterized by a relative increase in the molar concentration of terminal guanidine groups or terminal cyanoguardino groups. For example, in one embodiment, the biguanide composition comprises less than about 18 mole % of terminal amine groups and about 40 mol % or greater of terminal guanidine groups. In another embodiment, the biguanide composition comprises less than about 18 mole % of terminal amine groups and about 55 mol % or greater of terminal guanidine groups.

In this application, we refer to this biguanide composition as PHMB-CG*. We also refer to polymeric biguanide compositions in the generic sense as "hexamethylene biguanides", which one of ordinary skill in the art would recognize to include both PHMB as well as PHMB-CG*.

Representative examples of suitable quaternary ammonium compounds for use in the ophthalmic compositions of the present invention include, but are not limited to, poly[(dimethyliminio)-2-butene-1,4-diyl chloride] and [4-tris(2-hydroxyethyl)ammonio]-2-butenyl-w-[tris(2-hydroxyethyl)ammonio]-dichloride (chemical registry no. 75345-27-6) generally available as Polyquaternium 1 under the tradename ONAMER® M (Stepan Company, Northfield, Ill.), and the like and mixtures thereof.

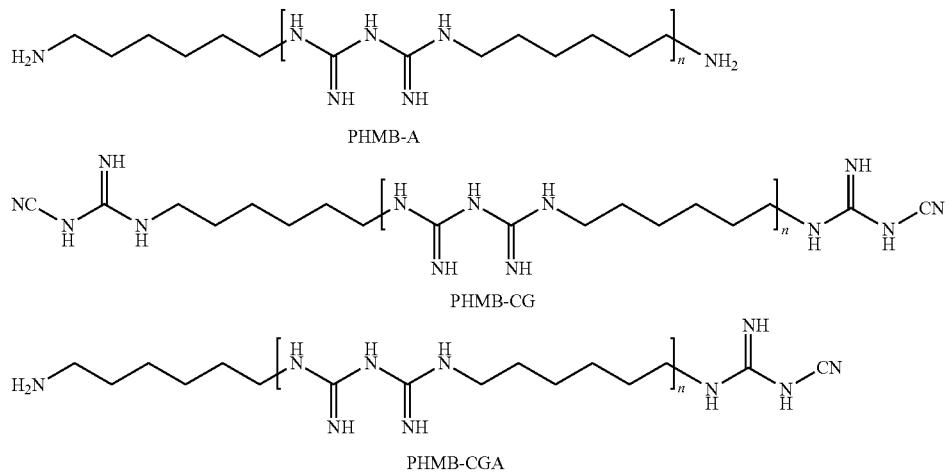

For each of these polymers, "n" represents the average number of repeating groups. Actually, a distribution of polymer length would exist for each of the polymers shown. The prior synthetic routes to PHMB provided a polymeric biguanide composition with about 50% by weight of the polymeric composition as PHMB-CGA, that is, having a cyanoguanidino end cap on one end and an amine on the other end, about 25% by weight PHMB-A and about 25% by weight PHMB-CG. Given this approximate weight ratio of the three Suitable terpene antimicrobial agents for use in the ophthalmic compositions of the present invention include any monoterpene, sesquiterpene and/or diterpene or derivatives thereof. Acyclic, monocyclic and/or bicyclic mono-, sesqui- and/or diterpenes, and those with higher numbers of rings, can be used. A "derivative" of a terpene as used herein shall be understood to mean a terpene hydrocarbon having one or more functional groups such as terpene alcohols, terpene ethers, terpene esters, terpene aldehydes, terpene ketones and the like and combinations thereof. Here, both the trans and also the cis isomers are suitable. The terpenes as well as the terpene moiety in the derivative can contain from 6 to about 100 carbon atoms and preferably from about 10 to about 25 carbon atoms.

Representative examples of suitable terpene alcohol antimicrobial agents include verbenol, transpinocarveol, cis-2-pinanol, nopol, isoborneol, carbeol, piperitol, thymol, α-terpineol, terpinen-4-ol, menthol, 1,8-terpin, dihydro-terpineol, nerol, geraniol, linalool, citronellol, hydroxycitronellol, 3,7-dimethyl octanol, dihydro-myrcenol, tetrahydro-alloocimenol, perillalcohol, falcarindiol and the like and mixtures thereof.

Representative examples of suitable terpene ether and terpene ester antimicrobial agents include 1,8-cineole, 1,4-cineole, isobornyl methylether, rose pyran, α-terpinyl methyl ether, menthofuran, trans-anethole, methyl chavicol, allocimene diepoxide, limonene mono-epoxide, isobornyl acetate, nonyl acetate, α-terpinyl acetate, linalyl acetate, geranyl acetate, citronellyl acetate, dihydro-terpinyl acetate, meryl acetate and the like and mixtures thereof.

Representative examples of terpene aldehyde and terpene ketone antimicrobial agents include myrtenal, campholenic aldehyde, perillaldehyde, citronellal, citral, hydroxy citronellal, camphor, verbenone, carvenone, dihydro-carvone, carvone, piperitone, menthone, geranyl acetone, pseudo-ionone, α-ionine, iso-pseudo-methyl ionone, n-pseudo-methyl ionone, iso-methyl ionone, n-methyl ionone and the like and mixtures thereof. Any other terpene hydrocarbons having functional groups known in the art may be used herein in the inventive composition.

In one embodiment, suitable terpenes or derivatives thereof as antimicrobial agents include, but are not limited to, tricyclene, α-pinene, terpinolene, carveol, amyl alcohol, nerol, β-santalol, citral, pinene, nerol, b-ionone, caryophillen (from cloves), guaiol, anisaldehyde, cedrol, linalool, d-limonene (orange oil, lemon oil), longifolene, anisyl alcohol, patchouli alcohol, α-cadinene, 1,8-cineole, ρ-cymene, 3-carene, ρ-8-mentane, trans-menthone, borneol, α-fenchol, isoamyl acetate, terpin, cinnamic aldehyde, ionone, geraniol (from roses and other flowers), myrcene (from bayberry wax, oil of bay and verbena), nerol, citronellol, carvacrol, eugenol, carvone, α-terpineol, anethole, camphor, menthol, limonene, nerolidol, farnesol, phytol, carotene (vitamin $A_1$), squalene, thymol, tocotrienol, perillyl alcohol, borneol, simene, carene, terpenene, linalool, 1-terpene-4-ol, zingiberene (from ginger) and the like and mixtures thereof.

In one embodiment, the compound of component (ii) of the ophthalmic composition comprises a branched, glycerol monoalkyl ether. In another embodiment, the compound of component (ii) of the ophthalmic composition comprises a branched, glycerol monoalkyl amine. In another embodiment, the compound of component (ii) of the ophthalmic composition comprises a branched, glycerol monoalkyl sulphide. In still another embodiment, the compound of component (ii) of the ophthalmic composition comprises any one mixture of a branched, glycerol monoalkyl ether, a branched, glycerol monoalkyl amine or a branched, glycerol monoalkyl sulphide.

In one embodiment, the branched, glycerol monoalkyl ether for use in the ophthalmic compositions of the present invention is 3-[(2-ethylhexyl)oxy]-1,2-propanediol (EHOPD). In another embodiment, the branched, glycerol monoalkyl amine is 3-[(2-ethylhexyl)amino]-1,2-propanediol (EHAPD). In another embodiment, the branched, glycerol monoalkyl sulphide is 3-[(2-ethylhexyl)thio]-1,2-propanediol (EHSPD). In still another embodiment, the ophthalmic composition comprises any one mixture of EHOPD, EHAPD and EHSPD. The chemical structures of EHOPD, EHAPD and EHSPD are provided below.

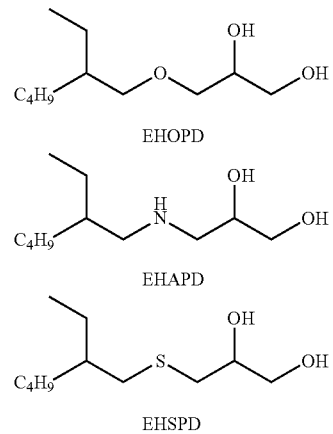

EHOPD is also referred to as octoxyglycerin and is sold under the tradename Sensiva® SC50 (Schülke & Mayr). EHOPD is a branched, glycerol monoalkyl ether known to be gentle to the skin, and to exhibit antimicrobial activity against a variety of Gram-positive bacteria such as *Micrococcus luteus, Corynebacterium aquaticum, Corynebacterium flavescens, Corynebacterium callunae*, and *Corynebacterium nephredi*. Accordingly, EHOPD is used in various skin deodorant preparations at concentrations between about 0.2 and 3 percent by weight. EHAPD can be prepared from 2-ethylhexylamine and 2,3-epoxy-1-propanediol using chemistry well known to those of ordinary skill in the art. EHSPD can be prepared from 2-ethylhexylthiol and 2,3-epoxy-1-propanediol using chemistry well known to those of ordinary skill in the art.

Suitable fatty acid monoester for use in the ophthalmic compositions of the present invention include those fatty acid monoesters comprising an aliphatic fatty acid portion having six to fourteen carbon atoms, and an aliphatic hydroxyl portion.

The term "aliphatic" refers to a straight or branched, saturated or unsaturated hydrocarbon having six to fourteen carbon atoms. In one embodiment, the aliphatic fatty acid portion is a straight chain, saturated or unsaturated hydrocarbon with eight to ten carbons. In another embodiment, the aliphatic fatty acid portion is a branched chain, saturated or unsaturated hydrocarbon with eight to ten carbons.

The aliphatic hydroxyl portion of the fatty acid monoester can be any aliphatic compound with at least one hydroxyl group. In many of the embodiments, the aliphatic hydroxyl portion will have from three to nine carbons. The aliphatic hydroxyl portion can include, but is not limited to, propylene glycol, glycerol, a polyalkylene glycol, e.g., polyethylene glycol or polypropylene glycol, a cyclic polyol, e.g., sorbitan, glucose, mannose, sucrose, fructose, fucose and inisitol and derivatives thereof, and a linear polyol, e.g., mannitol and sorbitol and derivatives thereof and the like and mixtures thereof.

Representative examples of suitable amidoamines for use in the ophthalmic compositions of the present inventions include those amidoamines of the general formula:

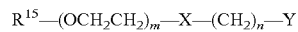

wherein $R^{15}$ is a is $C_6$-$C_{30}$ saturated or unsaturated hydrocarbon including by way of example, a straight or branched, substituted or unsubstituted alkyl, alkylaryl, or alkoxyaryl group; m is zero to 16; n is 2 to 16; X is —C(O)—$NR^{16}$— or —$R^{16}$N—C(O)—; Y is —$N(R^{17})_2$ wherein each of $R^{16}$ and $R^{17}$ independently are hydrogen, a $C_1$-$C_8$ saturated or unsaturated alkyl or hydroxyalkyl, or a pharmaceutically acceptable salt thereof.

Some of the amidoamines utilized in the present invention are available from commercial sources. For example, myristamidopropyl dimethylamine is available from Alcon Inc. (Fort Worth, Tx.) under the tradename Aldox®; lauramidopropyl dimethylamine is available from Inolex Chemical Company (Philadelphia, Pa.) under the tradename LEXAMINE® L-13; and stearamidopropyl dimethylamine is also available from Inolex Chemical Company as LEXAMINE® S-13. The above-described amidoamines can be synthesized in accordance with known techniques, including those described in U.S. Pat. No. 5,573,726.

The amount of the primary antimicrobial agent may vary depending on the specific agent employed. For the aforementioned organic nitrogen-containing agent, typically, such agents are present in concentrations ranging from about 0.00001 to about 0.5% weight percent, and more preferably, from about 0.00003% to about 0.05% weight percent. For sorbic acid, higher amounts may be required, typically about 0.01 to about 1 weight percent, more preferably about 0.1 to about 0.5 weight percent. It is preferred that the antimicrobial agent is used in an amount that will at least partially reduce the microorganism population in the formulations employed. If desired, the antimicrobial agent may be employed in a disinfecting amount, which will reduce the microbial bioburden by at least two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test-July, 1985 Contact Lens Solution Draft Guidelines).

The aqueous solutions may further contain one or more other components that are commonly present in ophthalmic solutions, for example, surfactants, tonicity adjusting agents; buffering agents; chelating agents; pH adjusting agents, viscosity modifying agents, and demulcents and the like as discussed hereinabove, and which aid in making ophthalmic compositions more comfortable to the user and/or more effective for their intended use.

The pH of the solutions and/or compositions according to the present invention may be maintained within the range of pH of about 4.0 to about 9.0, preferably about 5.0 to about 8.0, more preferably about 6.0 to about 8.0, and even more preferably about 6.5 to about 7.8. In one embodiment, pH values of greater than or equal to about 7 are most preferred.

According to one embodiment of the present, a method of treating a biomedical device involves contacting a biomedical device with the aqueous solution containing at least a hydrophilic reactive polymer. In another embodiment, a method involves immersing the biomedical device in the aqueous solution containing at least a hydrophilic reactive polymer; removing the device from the solution; packaging the biomedical device in a packaging solution in a manner preventing contamination of the device by microorganisms; and sterilizing the packaged solution and device. According to this embodiment, the packaging solution can be any packaging solution known in the art or, alternatively, a packaging solution containing a hydrophilic reactive polymer different than the solution in which the biomedical device was first immersed. In yet another embodiment, a method involves immersing the biomedical device in an aqueous solution containing at least a hydrophilic reactive polymer; packaging the solution containing the biomedical device in a packaging solution in a manner preventing contamination of the device by microorganisms; and sterilizing the packaged solution and device. In this embodiment, the solution containing the biomedical device can be stored "as is" in a packaging solution known in the art or, alternatively, in a packaging solution containing a hydrophilic reactive polymer as described herein which is different than the solution in which the biomedical device was immersed.

The following examples are provided to enable one skilled in the art to practice the invention and are merely illustrative of the invention. The examples should not be read as limiting the scope of the invention as defined in the claims.

In the example, the following abbreviations are used.

TRIS: tris(trimethylsiloxy)silylpropyl methacrylate

NVP: N-vinyl-2-pyrrolidone

HEMA: 2-hydroxyethyl methacrylate

HEMAVC: methacryloxyethyl vinyl carbonate

Vazo™ 64: a thermal polymerization initiator, said to be 2,2'-azobisisobutyronitrile (DuPont Chemicals, Wilmington, Del.)

IMVT: 1,4-bis(4-(2-methacryloxyethyl)phenylamino)anthraquinone

Example 1

Preparation of a Contact Lens

Mixtures were made by mixing the following components listed in Table 1, at amounts per weight.

TABLE 1

| Ingredient | Weight Percent |
|---|---|
| Polyurethane-siloxane prepolymer | 53 |
| TRIS | 15 |
| NVP | 33 |
| HEMA | 5 |
| HEMAVC | 1 |
| Boronic acid monomer | 1 |
| N-hexanol | 15 |
| Vazo-64 | 0.5 |
| IMVT | 150 ppm |

The resulting mixture is cast into contact lenses by introducing the mixture to a mold assembly composed of an ethyl vinyl alcohol mold for the anterior surface and an ethyl vinyl alcohol mold for the posterior surface and thermally curing the mixture at 100° C. for 2 hours. The resulting contact lens is released from the mold, extracted with isopropyl alcohol for 4 hours and placed in buffer solution. The boronic acid monomer used in this example is of the formula:

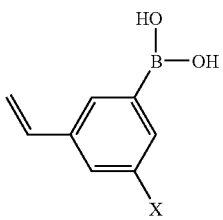

wherein X is —NO$_2$.

Examples 2-8 illustrate the syntheses of hydrophilic reactive polymers that can be used to link to the boronic acid moieties of the lens surface.

Example 2

Copolymer of DMA/GMA (86/14 mol/mol)

To a 1 L reaction flask were added distilled N,N-dimethylacrylamide (DMA, 48 g, 0.48 moles), distilled glycidyl methacrylate (GMA, 12 g, 0.08 moles) Vazo 64 initiator (AIBN, 0.1 g, 0.0006 moles) and anhydrous tetrahydrofuran (500 ml). The reaction vessel was fitted with a mechanical stirrer, condenser, thermal controller and a nitrogen inlet. Nitrogen was bubbled through the solution for 15 minutes to remove any dissolved oxygen. The reaction flask was then heated to 40° C. under a passive blanket of nitrogen for 168 hours. The reaction mixture was then added slowly to ethyl ether (1.5 L) with good mechanical stirring. The reactive polymer precipitated and organic solvents were decanted. The solid was collected by filtration and placed in a vacuum oven to remove the ether leaving 58.2 g of reactive polymer (97% yield). The reactive polymer was placed in a desiccator for storage until use.

Example 3

Copolymer of DMA/GMA (76/24 mol/mol)

To a 1 L reaction flask were added distilled N,N-dimethylacrylamide (DMA, 42 g, 0.42 moles), distilled glycidyl methacrylate (GMA, 18 g, 0.13 moles) Vazo 64 initiator (AIBN, 0.096 g, 0.0006 moles) and toluene (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The reactive polymer precipitated and was collected by vacuum filtration. The solid was placed in a vacuum oven at 30° C. overnight to remove the ether leaving 46.7 g of reactive polymer (78% yield). The reactive polymer was placed in a desiccator for storage until use.

Example 4

Copolymer of DMA/GMA (68/32 mol/mol)

To a 1 L reaction flask were added distilled N,N-dimethylacrylamide (DMA, 36 g, 0.36 moles), distilled glycidyl methacrylate (GMA, 24 g, 0.17 moles) Vazo 64 initiator (AIBN, 0.096 g, 0.0006 moles) and toluene (600 ml). The reaction vessel was fitted with a magnetic stirrer, condenser, thermal controller, and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The reactive polymer precipitated and was collected by vacuum filtration. The solid was placed in a vacuum oven at 30° C. overnight to remove the ether leaving 49.8 g of reactive polymer (83% yield). The reactive polymer was placed in a desiccator for storage until use.

Example 5

Copolymer of DMA/OFPMA/GMA (84/1.5/14.5 mol/mol/mol)

To a 3000 ml reaction flask were added distilled N,N-dimethylacrylamide (DMA, 128 g, 1.28 moles), 1H,1H,5H-octafluoropentylmethacrylate (OFPMA, 8 g, 0.024 moles), distilled glycidyl methacrylate (GMA, 32 g, 0.224 moles) Vazo-64 initiator (AIBN, 0.24 g, 0.00144 moles) and tetrahydrofuran (2000 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 12 L of ethyl ether with good mechanical stirring. The reactive polymer precipitated and was collected by vacuum filtration. The solid was placed in a vacuum oven at 30° C. overnight to remove the ether leaving 134.36 g of reactive polymer (80% yield). The reactive polymer was placed in a desiccator for storage until use.

Example 6

Copolymer of DMA/OFPMA/GMA (85/0.18/14.82 mol/mol/mol)

To a 500 ml reaction flask were added distilled N,N-dimethylacrylamide (DMA, 16 g, 0.16 moles), 1H,1H,5H-octafluoropentylmethacrylate (OFPMA, 0.1 g, 0.0003 moles, used as received), distilled glycidyl methacrylate (GMA, 4 g, 0.028 moles) Vazo-64 initiator (AIBN, 0.063 g, 0.00036 moles) and tetrahydrofuran (300 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 3 L of ethyl ether with good mechanical stirring. The reactive polymer precipitated and was collected by vacuum filtration. The solid was placed in a vacuum oven at 30° C. overnight to remove the ether leaving 14.5 g of reactive polymer (69 yield). The reactive polymer was placed in a desiccator for storage until use.

Example 7

Copolymer of DMA/LMA/GMA (84/1.5/14.5 mol/mol/mol)

To a 1000 ml reaction flask were added distilled N,N-dimethylacrylamide (DMA, 32 g, 0.32 moles), laurylmethacrylate (LMA, 1.5 g, 0.006 moles, used as received), distilled glycidyl methacrylate (GMA, 8 g, 0.056 moles) Vazo-64 initiator (AIBN, 0.06 g, 0.00036 moles) and tetrahydrofuran (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 3 L of ethyl ether with good mechanical stirring. The reactive polymer precipitated and was collected by vacuum filtration. The solid was placed in a vacuum oven at 30° C. overnight to remove the ether leaving 29.2 g of reactive polymer (70% yield). The reactive polymer was placed in a desiccator for storage until use.

Example 8

Copolymer of NVP/VCHE (85/15 mol/mol)

To a 1 L reaction flask were added distilled N-vinyl-2-pyrrolidinone (NVP, 53.79 g, 0.48 moles), 4-vinylcyclohexyl-1,2-epoxide (VCHE, 10.43 g, 0.084 moles), Vazo 64 (AIBN, 0.05 g, 0.0003 moles) and THF (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The copolymer precipitated and was collected by vacuum filtration. The solid was placed in a vacuum oven at 30° C. overnight to remove the ether leaving 21 g of reactive polymer (a 32% yield). The reactive polymer was placed in a desiccator for storage until use.

Example 9

For coating with the hydrophilic reactive polymers of Examples 2-8, each lens of Example 1 is placed in polypropylene contact lens blister packs containing a buffered saline solution of a hydrophilic reactive polymer of Examples 2-8. The blisters are sealed and autoclaved at 121° C. for 30 minutes.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A biomedical device including a shaped article that is a polymerization product of a monomeric mixture comprising (i) a polymerizable monomer containing a boronic acid moiety and an electron withdrawing moiety; and (ii) a biomedical device-forming comonomer; said biomedical device including, on a surface of said shaped article, a hydrophilic reactive polymer having complementary reactive functionalities along the polymer chain, wherein the complementary reactive functionalities along the polymer chain of the hydrophilic reactive polymer bind the boronic acid moieties of the shaped article, thereby producing a biocompatible coating which can be removed and re-applied to restore the surface properties of the biomedical device to, and wherein the hydrophilic reactive polymer is selected from the group consisting of a copolymer derived from 2-vinyl-4,4-dimethyl-2-oxazolin-5-one and dimethylacrylamide, and a copolymer obtained by hydrolyzing a polymerization product of a monomer mixture comprising an ethylenically unsaturated epoxy-containing monomer.

2. The biomedical device of claim 1, wherein the electron withdrawing moiety is —$CF_3$, —$NO_2$, —F, —Cl or —Br.

3. The biomedical device of claim 1, wherein the polymerizable monomer containing a boronic acid moiety and an electron withdrawing moiety comprises a polymerizable ethylenically unsaturated containing aryl boronic acid.

4. The biomedical device of claim 1, wherein the polymerizable monomer containing a boronic acid moiety is derived from 3-vinylphenylboronic acid or 3-methacrylamidophenylboronic acid.

5. The biomedical device of claim 1, wherein the biomedical device-forming comonomer is a silicone-containing monomer.

6. The biomedical device of claim 1, wherein the monomeric mixture further comprises at least one member selected from the group consisting of a hydrophilic monomer and a hydrophobic monomer.

7. The biomedical device of claim 6, wherein the hydrophilic monomer is selected from the group consisting of an unsaturated carboxylic acid, vinyl lactam, amide, polymerizable amine, vinyl carbonate, vinyl carbamate, oxazolone monomer and mixtures thereof.

8. The biomedical device of claim 6, wherein the hydrophilic monomer is selected from the group consisting of 2-hydroxyethylmethacrylate, 2-hydroxyethylacrylate, glyceryl methacrylate, N-vinyl pyrrolidone, N-vinyl-N-methyl acetamide, N,N-dimethyl methacrylamide, N,N-dimethylacrylamide, acrylic acid, methacrylic acid and mixtures thereof.

9. The biomedical device of claim 1, wherein component (i) comprises about 0.1 to about 10 weight percent of the mixture and the biomedical device-forming comonomer component (ii) comprises about 5 to about 20 weight percent of the mixture.

10. The biomedical device of claim 1, wherein the hydrophilic reactive polymer is a copolymer derived from 2-vinyl-4,4-dimethyl-2-oxazolin-5-one and dimethylacrylamide.

11. The biomedical device of claim 1, wherein the hydrophilic reactive polymer is a copolymer obtained by hydrolyzing a polymerization product of a monomer mixture comprising an ethylenically unsaturated epoxy-containing monomer.

12. The biomedical device of claim 11, wherein the copolymer further comprises monomeric units derived from a hydrophilic monomer selected from the group consisting of an aprotic hydrophilic monomer, protic hydrophilic monomer and mixtures thereof.

13. The biomedical device of claim 12, wherein the aprotic hydrophilic monomer is selected from the group consisting of N,N-dimethylacrylamide, N,N-dimethyl methacrylamide, N-methylmethacrylamide, N-methylacrylamide, N-vinylpyrrolidinone, methoxypolyoxyethylene methacrylates and mixtures thereof.

14. The biomedical device of claim 12, wherein the protic hydrophilic monomer is selected from the group consisting of methacrylic acid, 2-hydroxyethyl methacrylate and mixtures thereof.

15. The biomedical of claim 1, wherein the biomedical device is in the form of a contact lens.

* * * * *